US010238097B2

(12) United States Patent
Sharma et al.

(10) Patent No.: US 10,238,097 B2
(45) Date of Patent: Mar. 26, 2019

(54) CANDLE DISPENSER

(71) Applicant: S.C. Johnson & Son, Inc., Racine, WI (US)

(72) Inventors: Nitin Sharma, Kenosha, WI (US); Brian T. Davis, Burlington, WI (US); Allyce M. Gilligan, Milwaukee, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 604 days.

(21) Appl. No.: 14/289,761

(22) Filed: May 29, 2014

(65) Prior Publication Data

US 2015/0342172 A1  Dec. 3, 2015

(51) Int. Cl.

| A01M 29/12 | (2011.01) |
|---|---|
| A01M 1/00 | (2006.01) |
| A61L 9/03 | (2006.01) |
| A61L 9/01 | (2006.01) |
| F21V 35/00 | (2006.01) |
| A01M 1/20 | (2006.01) |
| A01M 29/14 | (2011.01) |

(52) U.S. Cl.
CPC .......... *A01M 1/2088* (2013.01); *A01M 29/12* (2013.01); *A01M 29/14* (2013.01); *A61L 9/03* (2013.01)

(58) Field of Classification Search
CPC .................................................. A01M 29/12
USPC ....................................................... 422/135
See application file for complete search history.

(56) References Cited

U.S. PATENT DOCUMENTS

| 4,781,895 A | 11/1988 | Spector |
| 6,482,365 B1 | 11/2002 | Soller |
| 6,534,079 B1 * | 3/2003 | Munagavalasa ....... A01N 53/00 424/409 |

(Continued)

FOREIGN PATENT DOCUMENTS

| FR | 1 404 904 A | 7/1965 |
| FR | 2 294 717 A1 | 7/1976 |

OTHER PUBLICATIONS

International Search Report and Written Opinion of the International Searching Authority issued in PCT Application No. PCT/US2015/032101, dated Nov. 16, 2015, 19 pages.

*Primary Examiner* — Kevin Joyner
*Assistant Examiner* — Holly M Mull
(74) *Attorney, Agent, or Firm* — Quarles & Brady LLP (57) ABSTRACT

Devices for dispensing an air treatment chemical such as insect repellent are disclosed. There is a chimney housing having a side wall defining an internal cavity. There is also a caddy assembly supported by the housing and having an upper caddy frame configured to mount a substrate bearing an air treatment chemical adjacent an upper portion of the housing, and a candle holder coupled to the upper caddy frame and configured to support a candle having a wick adjacent a lower portion of the housing. There is also a substrate bearing air treatment chemical suitable to be supported by the upper caddy frame, and a candle suitable to be supported by the candle holder. A refill kit for such devices is also disclosed. Also disclosed is an embodiment with a sand core bearing the repellent, a heat deflector positioned under the sand core, and a candle positioned under the heat deflector.

19 Claims, 12 Drawing Sheets

(56) References Cited

U.S. PATENT DOCUMENTS

| | | | |
|---|---|---|---|
| 6,663,838 B1* | 12/2003 | Soller | A01M 1/2088 |
| | | | 422/120 |
| 7,138,130 B2 | 11/2006 | Davis et al. | |
| 7,820,188 B2 | 10/2010 | Varanasi et al. | |
| 8,047,837 B2 | 11/2011 | Furner et al. | |
| 2003/0067770 A1* | 4/2003 | Bonnema | B44C 5/005 |
| | | | 362/186 |
| 2006/0039945 A1* | 2/2006 | Davis | A01M 1/2077 |
| | | | 424/409 |
| 2008/0110450 A1* | 5/2008 | Wu | A61L 9/03 |
| | | | 126/256 |
| 2009/0004614 A1 | 1/2009 | Furner et al. | |
| 2012/0251962 A1 | 10/2012 | White | |
| 2014/0010715 A1* | 1/2014 | Furner | A61L 9/037 |
| | | | 422/125 |

* cited by examiner

CANDLE DISPENSER

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to devices that dispense air treatment chemicals ("actives") from a substrate using the heat of a candle to drive the dispensing. More particularly, the invention relates to such devices that dispense the active over a prolonged period in a relatively consistent manner that provides effective coverage throughout an area such as an outdoor patio.

A variety of devices are known for dispensing volatilizable air treatment chemicals such as pest control materials (e.g., insecticides, insect repellants, or insect growth control regulators), air scents or deodorizers (e.g., masks), allergen control ingredients, disinfectants, sanitizers or other materials. In some of these devices the air treatment chemical is mixed with candle wax and is dispensed during candle burning (where the chemical is released primarily from the heated wax surrounding the wick). While this is a common technique for dispensing a variety of fragrances, typically it has been less successful when dispensing certain particularly desirable pest control materials.

Attempts have been made to use heat from a candle to distribute air treatment chemicals from an adjacent impregnated pad surface. See e.g., U.S. Pat. Nos. 4,781,895, 7,138,130 and 8,047,837. However, it is difficult to design such devices to work over a four hour, six hour or even longer period (four to six hours being a typical period for a dinner party or picnic) while consistently distributing enough chemical to be effective in a large area throughout that period.

Some attempts have been made to use electrical heaters to drive air treatment chemicals in a more controlled manner from a substrate or reservoir. See U.S. Pat. No. 7,820,188. However, such systems required structures to generate, store, and/or accommodate electrical power, which increases the cost of the device.

U.S. patent application publication 2012/0251962 taught a trapeze-like structure for lowering a candle into a glass chimney, but was not directed to dispensing a volatizable air treatment chemical.

Thus, a need exists for low cost air treatment chemical dispensers where heat drives an air treatment chemical off of a carrier substrate in a way which provides prolonged useful life and capability of treating a large area.

BRIEF SUMMARY OF THE INVENTION

In one aspect the invention provides a device for dispensing an air treatment chemical. There is a housing (e.g. a chimney) having a side wall defining an internal cavity, a caddy assembly supported by the housing and having an upper caddy frame configured to mount a substrate bearing an air treatment chemical adjacent an upper portion of the housing and a candle holder coupled to the upper caddy frame and configured to support a candle having a wick adjacent a lower portion of the housing in the internal cavity. There is also the substrate bearing the air treatment chemical configured to be suitable to be supported by the upper caddy frame, and a candle suitable to be supported by the candle holder.

In preferred forms there is also a heat deflector plate arranged between the substrate and candle holder. The plate has a vent structure so that it both deflects heat and allows air passage there through.

In other preferred aspects of the invention there is also a base coupled to the housing that can align the candle holder with respect to the housing, and the housing has a wide upper portion, a middle portion less wide than the upper portion, and a lower portion more wide than the middle portion.

In the most preferred forms the candle can be easily installed (or removed for replacement) from above (as the candle holder is suspended by a trapeze-like hanger system from the upper caddy frame). There may also be a refill frame for supporting the substrate (so a consumer doesn't need to contact the substrate when installing it above the candle). In this form the heat deflector plate can be supported by the upper caddy below the refill frame.

In other preferred forms the device is for controlling insects like mosquitoes, the air treatment chemical is pest control active ingredient, and the device is configured so that the substrate can release at least 6 mg per hour of the air treatment chemical when the candle is lit.

Most particularly the distance of the substrate bottom from the wick has been set, taking into account the heat deflector, so that the candle can heat a bottom of the substrate for over a consecutive hour to between 115 degrees C. and 160 degrees C., and when this occurs a top of the substrate can be maintained between 115 degrees C. and 135 degrees C. throughout that hour. When using a sand core/binder resin substrate this yields a surprisingly steady dispensing of active over a period of one or more hours.

In another aspect the invention provides a refill kit for a device to dispense an air treatment chemical (e.g. pest control active ingredient). The kit has a substrate supported on a frame, the substrate being in the form of a puck. The substrate comprises sand, a binder, and an air treatment chemical. There is also a candle suitable to heat the substrate.

In preferred forms the frame further comprises a retainer that inhibits removal of the substrate from the frame, there is an array of vents as part of the refill frame, and the refill frame has a lift handle. In other preferred forms the air treatment chemical is a pest control active ingredient, and the length of time the candle burns is essentially the same as the length of time the air treatment chemical is released at effective levels when heated by the candle.

In yet other forms the invention can provide a device for dispensing a pest control active ingredient. This can have a sand core substrate impregnated with the pest control active ingredient, a candle positioned below the sand core substrate, and a heat deflector plate positioned between the substrate and the candle, the heat deflector plate having a plurality of vent holes. When in use the temperature of the top surface of the sand core substrate can average over an hour period at 115 degrees C. to 135 degrees C.

In preferred forms there is also a housing having a side wall defining an internal cavity, and a caddy assembly. The caddy assembly has an upper caddy frame configured to mount the substrate adjacent an upper portion of the housing, and a candle holder coupled to the upper caddy frame and configured to support the candle adjacent a lower portion of the housing.

If desired the upper caddy frame has a first internal circumference geometry configured to accommodate the shape of a refill frame supporting the substrate, the candle holder has a second internal circumference geometry configured to accommodate the shape of the candle, and the first internal circumference geometry differs in shape from the second internal circumference geometry. Also, the heat deflector plate comprises aluminum, and the plurality of vent holes are arranged either with generally uniform sized holes or with smaller holes toward a center of the plate and larger holes positioned radially outwardly from the smaller holes.

Most preferably the distance between a top of the candle and a bottom of the substrate (see e.g. "A" in FIG. 2) is from 60 mm to 105 mm, the caddy has two handles, and a top of the housing has two recesses adapted to receive the handles when the caddy is lowered into the internal cavity of the housing.

When the wick is lit a resulting flame will heat the substrate and thereby cause the air treatment chemical to be dispensed from the substrate. The candle is hung by the hanger to facilitate positioning of the candle below the substrate (and replacement of the candle).

In other forms the housing may have at least one air inlet adjacent a lower portion of the housing and a bottom wall with at least one alignment fin for positioning a lower portion of the candle holder.

Long term effective dispensing has been achieved where the substrate is frustum (essentially puck) shaped and dosed with 25 mg or more of a pest control active ingredient such as metofluthrin, a distance from a top of the wick to a bottom of the substrate is between 60 mm and 105 mm, and the candle is configured to be able to heat a bottom of the substrate for over a consecutive hour to between 115 degrees C. and 160 degrees C. and when this occurs a top of the substrate can be maintained between 115 degrees C. and 135 degrees C. throughout that hour. The device can effectively control mosquitoes in a relatively large area (e.g. a patio of 100 square feet or more) for four consecutive hours, or even six consecutive hours.

The candle may comprise a mix of conventional candle waxes, and a cotton wick, and the substrate may be between 0.5 and 5 cm thick (e.g., 1 cm) at its thickest point. The substrate may be dosed with 25 mg or more of a mosquito control chemical as the pest control active ingredient, and a distance from a top of the wick to the bottom of the substrate may be between 60 mm and 105 mm. By constructing the device with these parameters surprising control and extended life have been achieved.

The candle is supported adjacent one or more air vents. This allows the candle to be fed with enough fresh air to generate sufficient heat to reach these heating levels. In the most preferred embodiments the candle is hung from a hanger connected to or integral with a caddy having a lift handle such that the candle can be positioned in the housing by lowering it down via the lift handle, and replaced by lifting the candle up via the lift handle. In yet other forms, the size and number of apertures in, and thickness of, a heat deflector, and the material the deflector is made of, can be varied to provide other types of control over the temperature that the sand core is exposed to.

Because the upper carrier structure has a lift handle, which enables the refill to be lifted away from the candle housing so as to facilitate replacement when the substrate is used up, this results in a savings in that at least the candle housing and supporting hanger structure can be used with multiple refills.

A porous sand core permits the active to quickly migrate to an upper part of the substrate in the presence of candle heat. Surprisingly, the preferred sand/binder core is resistant to releasing significant amounts of active when not heated, thereby permitting a consumer to use a single refill on multiple days without having to hermetically seal the device between uses. This also helps reduce the cost of packaging when the product is first sold.

From the discussion below it will be appreciated that various embodiments of the invention achieve a variety of advantages. As these embodiments are merely illustrative, they are not intended to represent the full scope of the invention. Thus, reference should therefore be made to the claims herein for interpreting the full scope of the invention.

DETAILED DESCRIPTION OF THE PREFERRED EMBODIMENTS

Figure 1A:
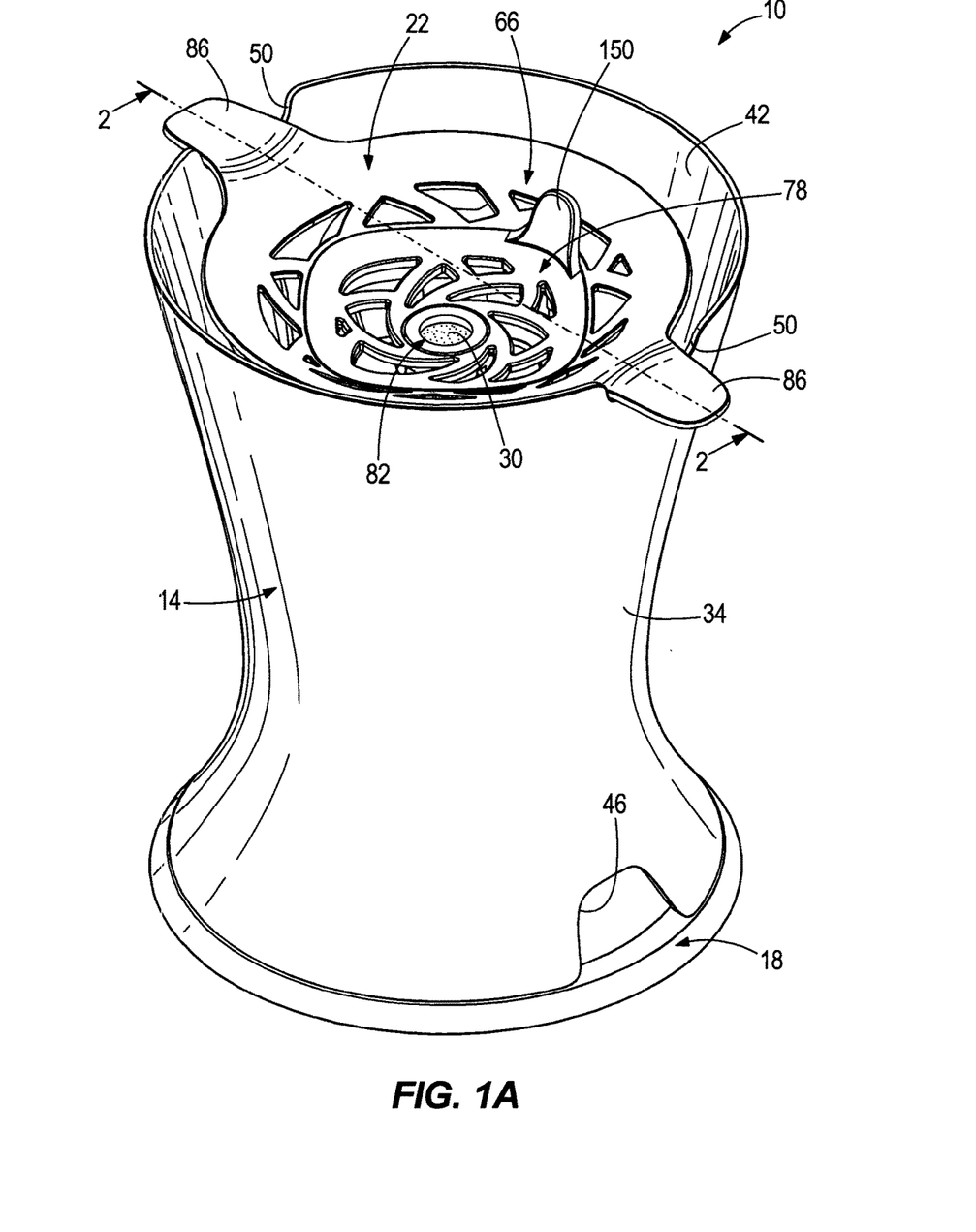
FIG. 1A is an upper perspective view of a candle dispenser of the present invention, where the outer chimney is translucent.
Figure 1B:
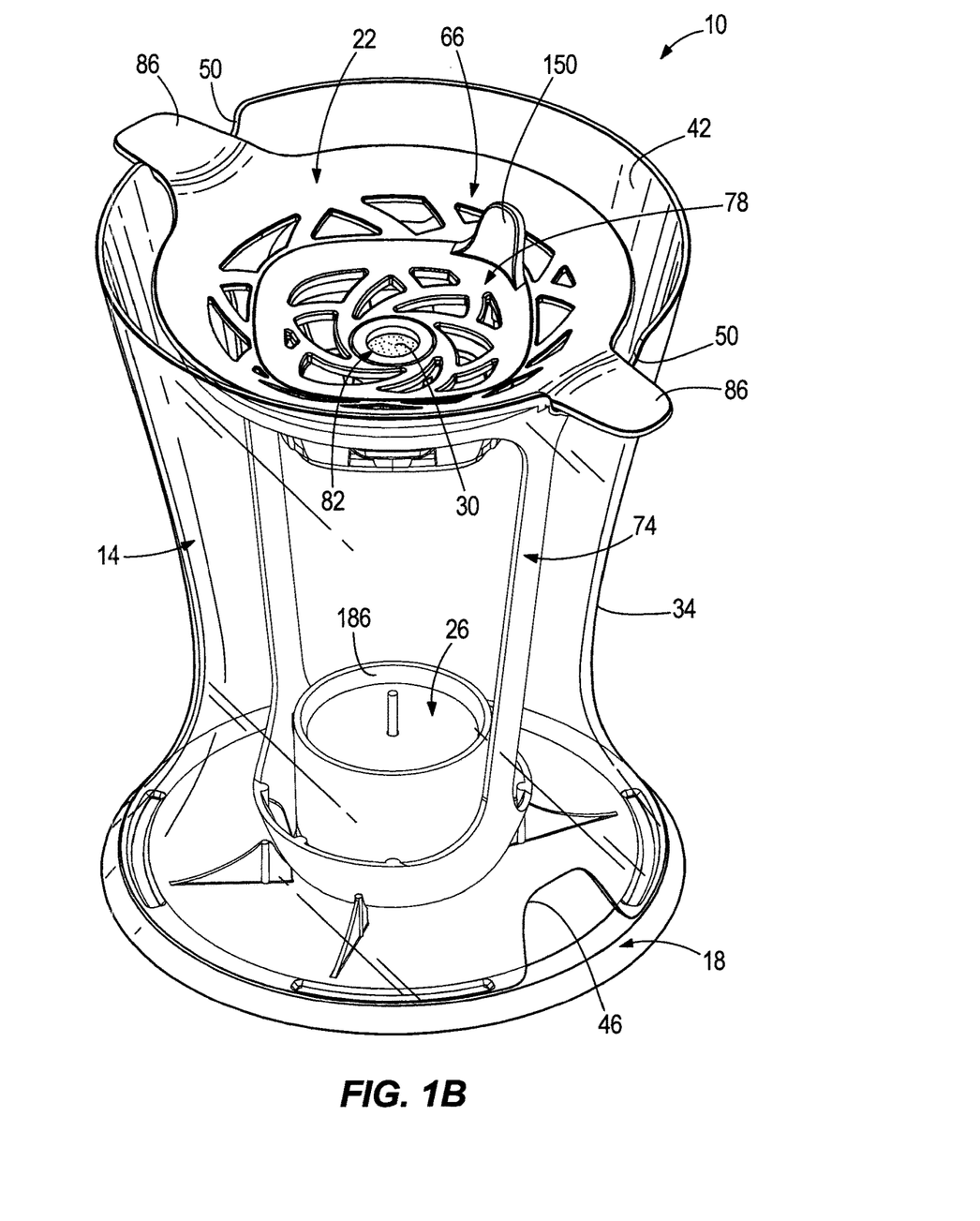
FIG. 1B is a view identical to FIG. 1A, but where the outer chimney is transparent.
Figure 2:
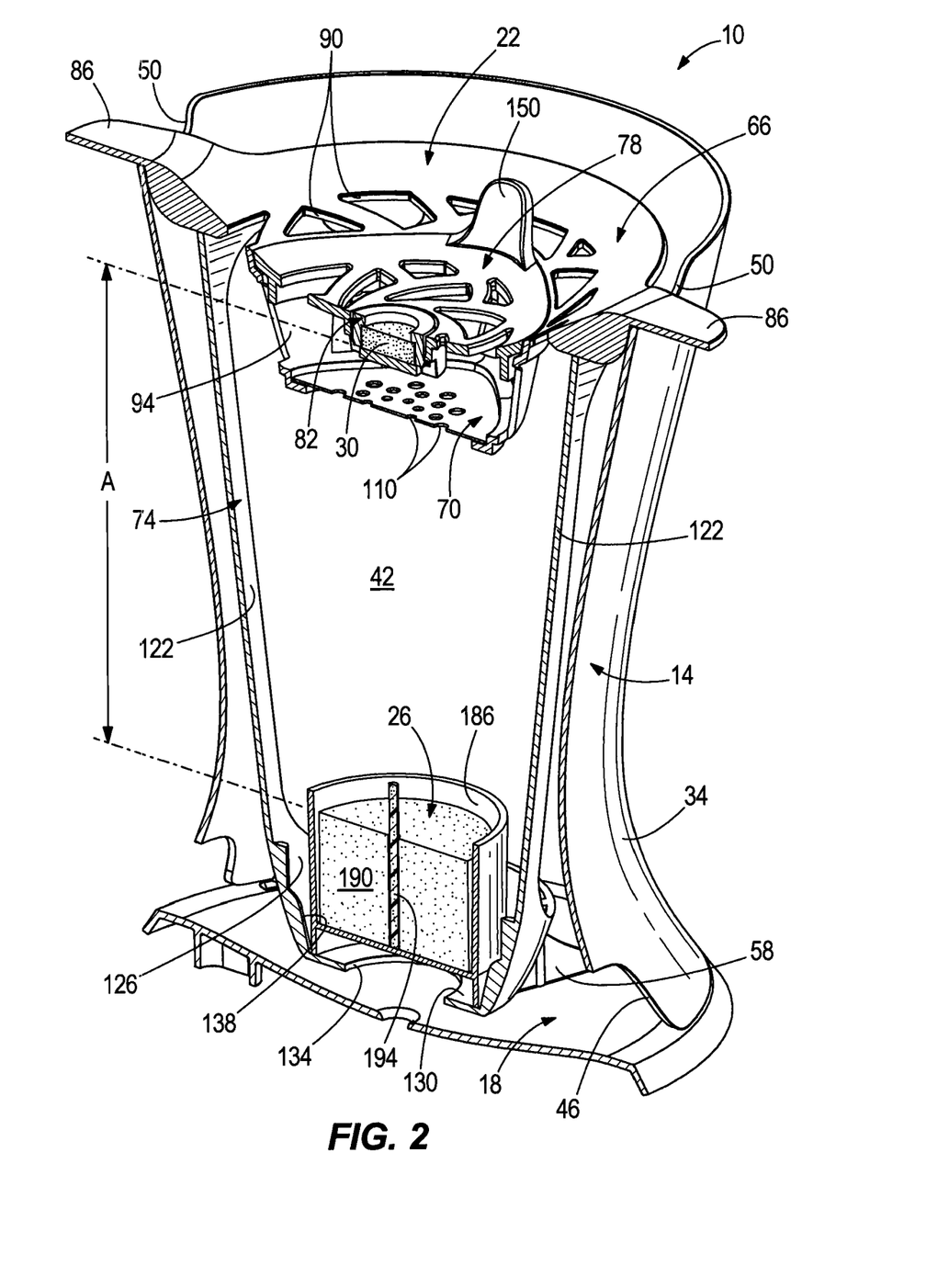
FIG. 2 is a sectional view of the candle dispenser of FIG. 1, taken along line 2-2 of FIG. 1.
Figure 3:
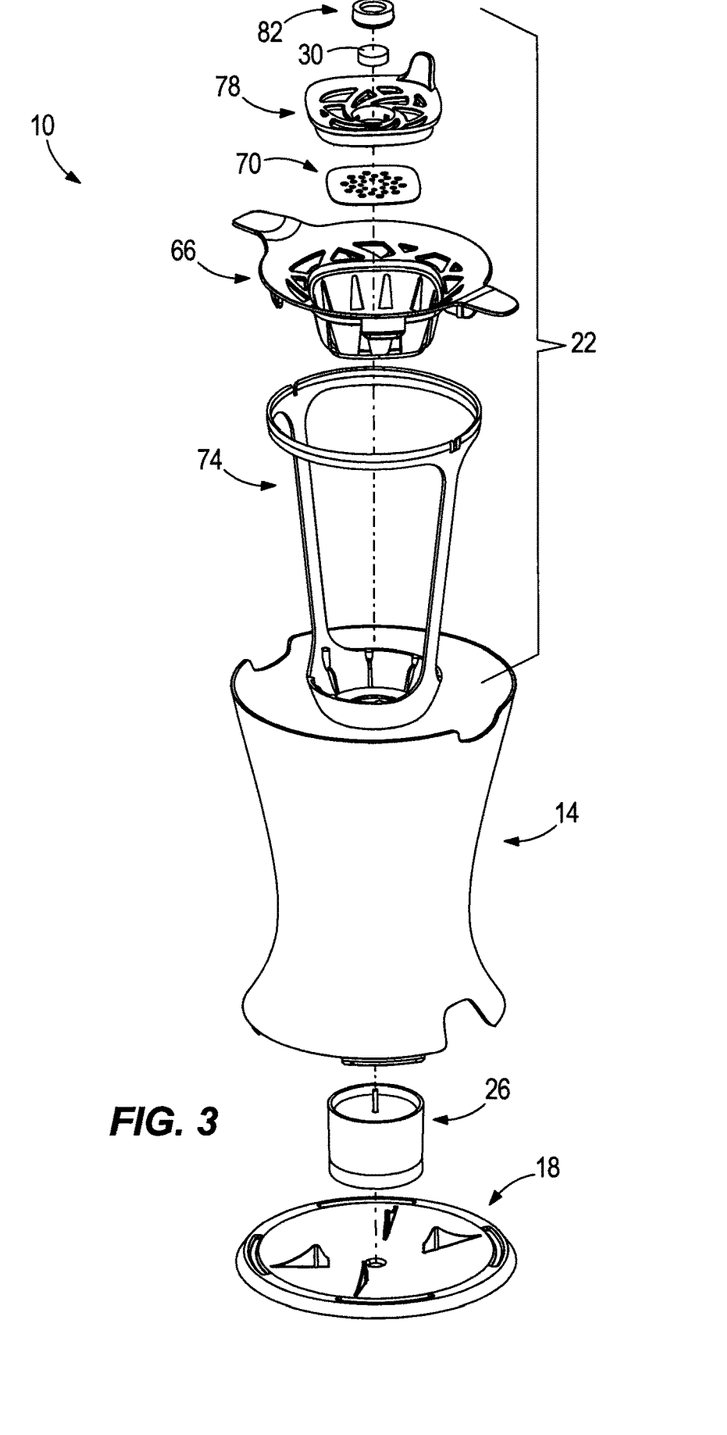
FIG. 3 is an exploded view of the candle dispenser of FIG. 1.

FIGS. 1-3 shows a device in the form of a candle dispenser 10 for dispensing air treatment chemical. The candle dispenser 10 includes a housing 14, a base 18, and an upper caddy 22. With reference to FIG. 2, the upper caddy 22 holds a heat source in the form of a candle 26 and a substrate 30. As shown in FIG. 1B the housing 14 can alternatively be a transparent housing.

Figure 4:
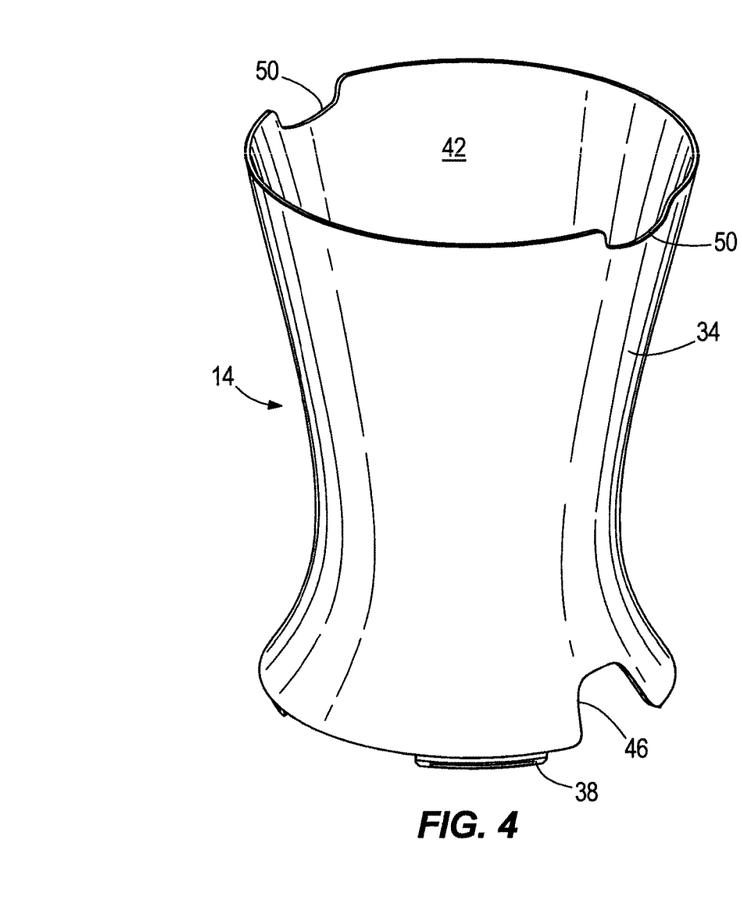
FIG. 4 is an upper perspective view of the housing of the candle dispenser of FIG. 1.
Figure 5:
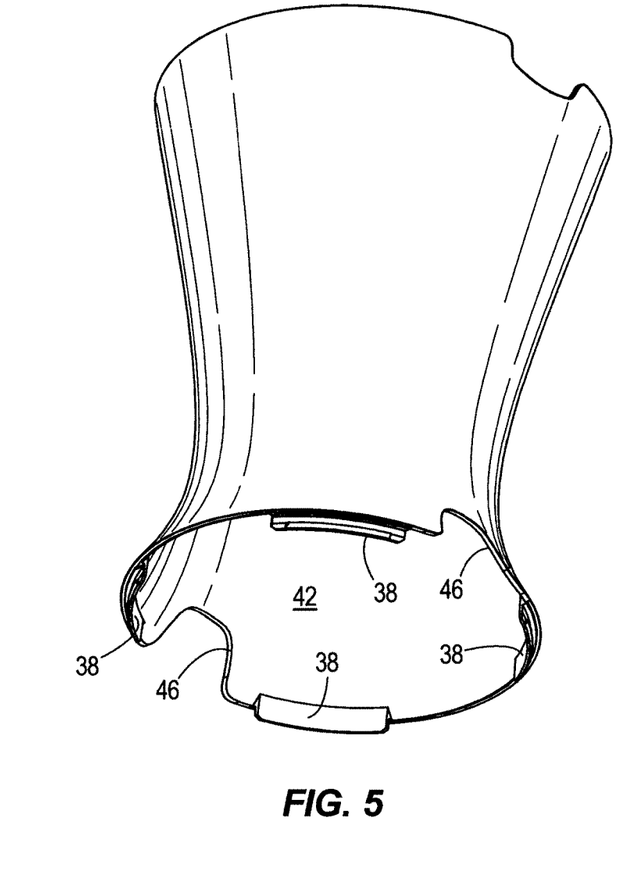
FIG. 5 is a lower perspective view of the FIG. 4 housing.

As shown in FIGS. 4 and 5, the housing 14 is generally sleeve-shaped and may be referred to as a shade or a chimney. The housing 14 includes a substantially hyperbolic shaped side wall 34 with a curvature and a base engaging structure in the form of four tabs 38. The side wall 34 defines an interior cavity 42 with an open top, an air inlet in the form of two bottom vents 46, and a caddy mounting feature in the form of two caddy recesses 50. The housing 14 may be made of glass or another heat-resistant transparent or translucent material, such as a plastic. A translucent housing 14 would ornamentally hide portions of the upper caddy 22 and structures depending from it, but show light generated from the candle 26.

In other embodiments the base engaging structure may include more or less than four tabs 38, or may be defined by recesses slots, fasteners, or another structure. The air inlet may include more or less than two bottom vents 46 or the air inlet may be spaced a distance from a bottom of the housing 14, as desired. The caddy mounting feature may engage the caddy 22 differently. For example, the caddy mounting feature could include pins, apertures, or another feature, as desired.

Figure 6:
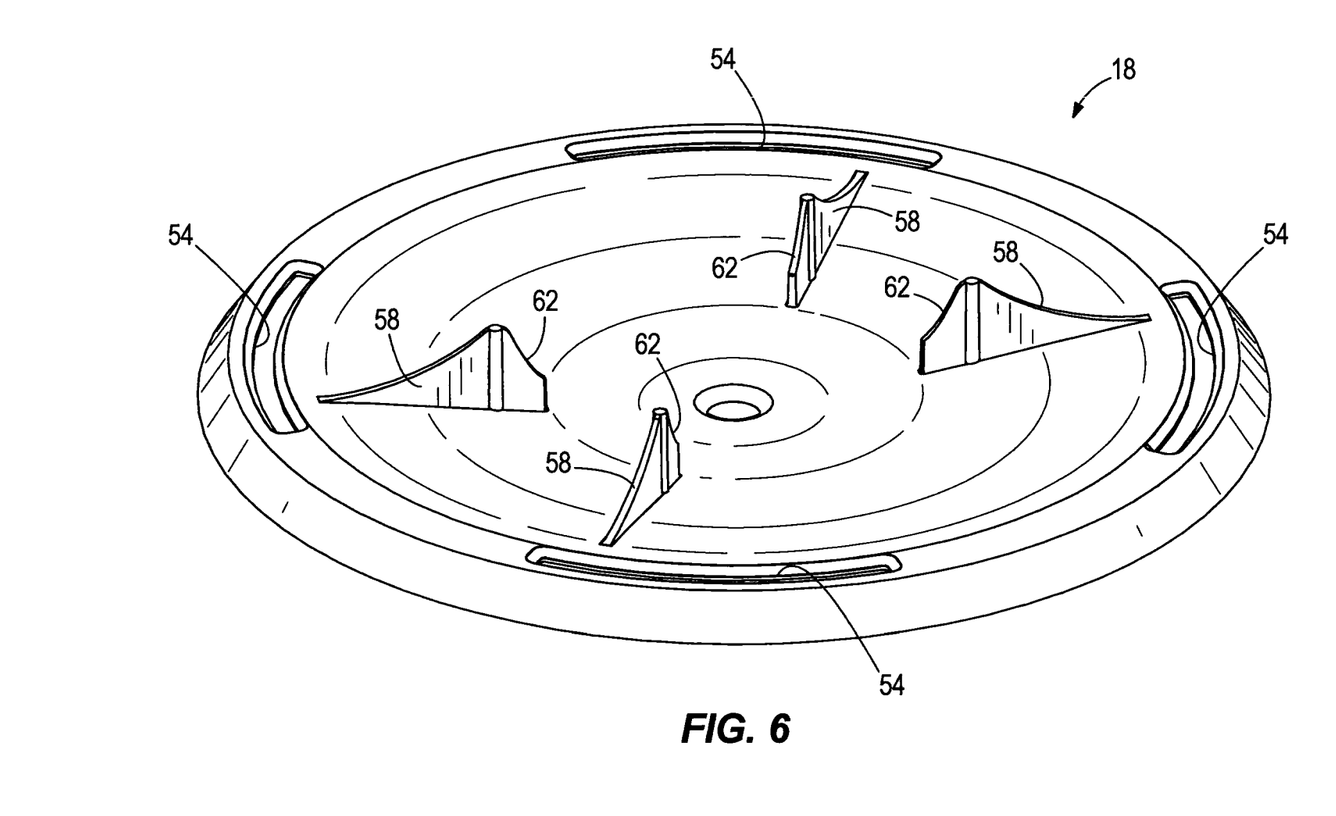
FIG. 6 is an upper perspective view of a base of the candle dispenser of FIG. 1.

As shown in FIG. 6, the base 18 includes a housing engaging structure in the form of recesses 54 sized to receive the tabs 38 of the housing 14. The recesses 54 and tabs 38 are arranged such that the tabs 38 snap into the recesses 54 and maintain the housing 14 attached to the base 18. The base 18 further includes a caddy centering feature in the form of four fins 58. Each fin 58 defines a shaped profile 62 shaped to engage and center the caddy 22 relative to the base 18. The base 18 is also arranged to support the candle dispenser 10 on a surface.

Figure 7:
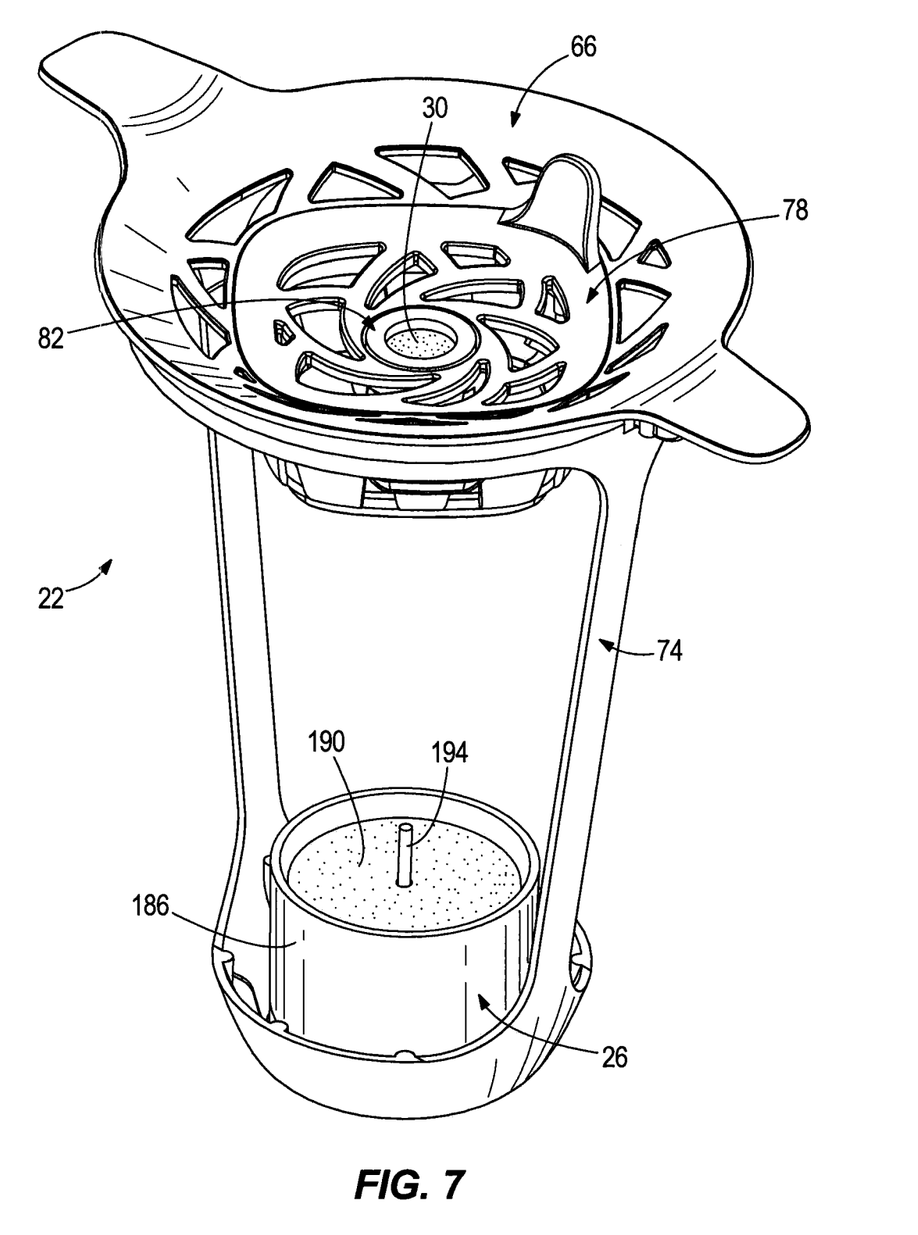
FIG. 7 is an upper perspective view of a caddy assembly of the candle dispenser of FIG. 1, with a candle and refill frame mounted thereon.
Figure 12:
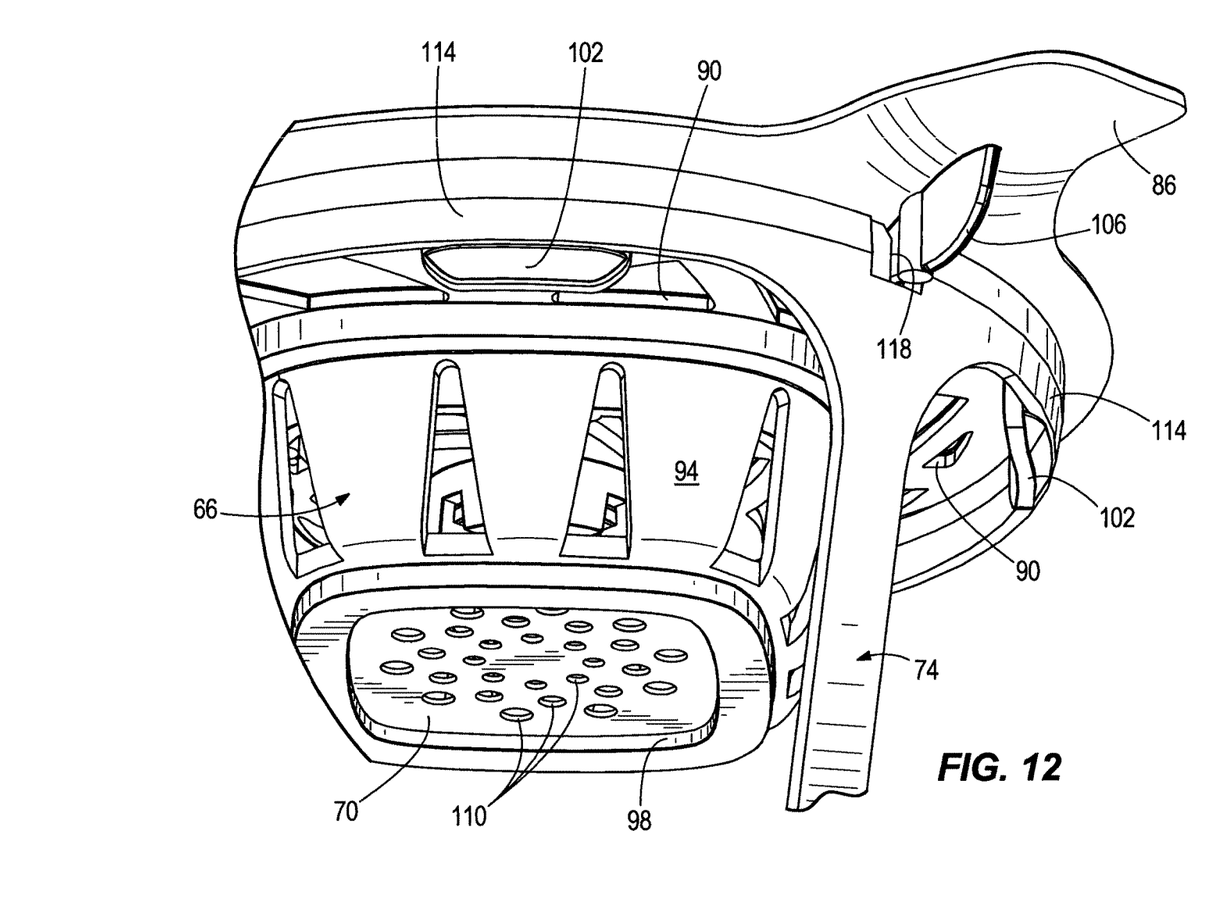
FIG. 12 is an enlarged lower perspective detail view of a portion of the FIG. 7 caddy assembly.

As shown in FIGS. 7 & 12, the caddy 22 includes an upper caddy frame 66, a heat deflector plate 70, lower caddy frame 74 with hanger elements 122, and a candle holder 126, into which the user inserts a candle 26, and a refill frame 78 supporting a substrate 30, preferably including a refill retainer 82.

Figure 8:
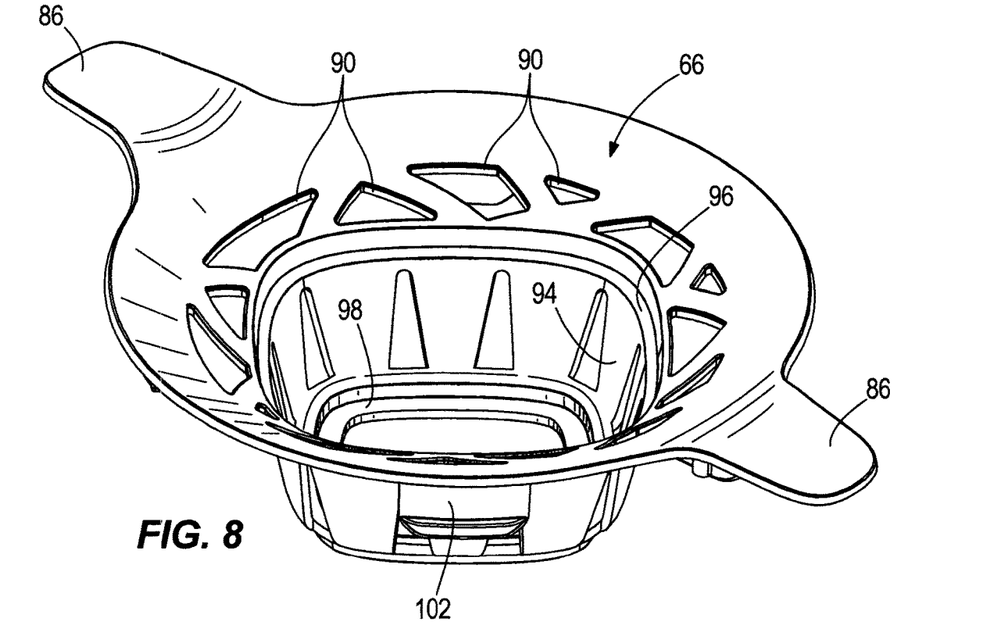
FIG. 8 is an upper perspective view of an upper caddy frame portion of the caddy assembly of FIG. 7.

Turning to FIG. 8, the upper caddy frame 66 includes a housing mounting feature in the form of two lift handles 86 sized to engage the caddy recess 50 of the housing 14. A plurality of vents 90 are formed around a top periphery of the upper caddy frame 66 and are arranged to allow a predetermined airflow therethrough while the candle dispenser 10 is functioning. The upper caddy frame 66 includes a refill receiving feature in the form of a cavity 94 that is sized to receive the refill frame 78 and defines shoulder 96 and a heat deflector engaging structure in the form of a rim 98.

Figure 9:
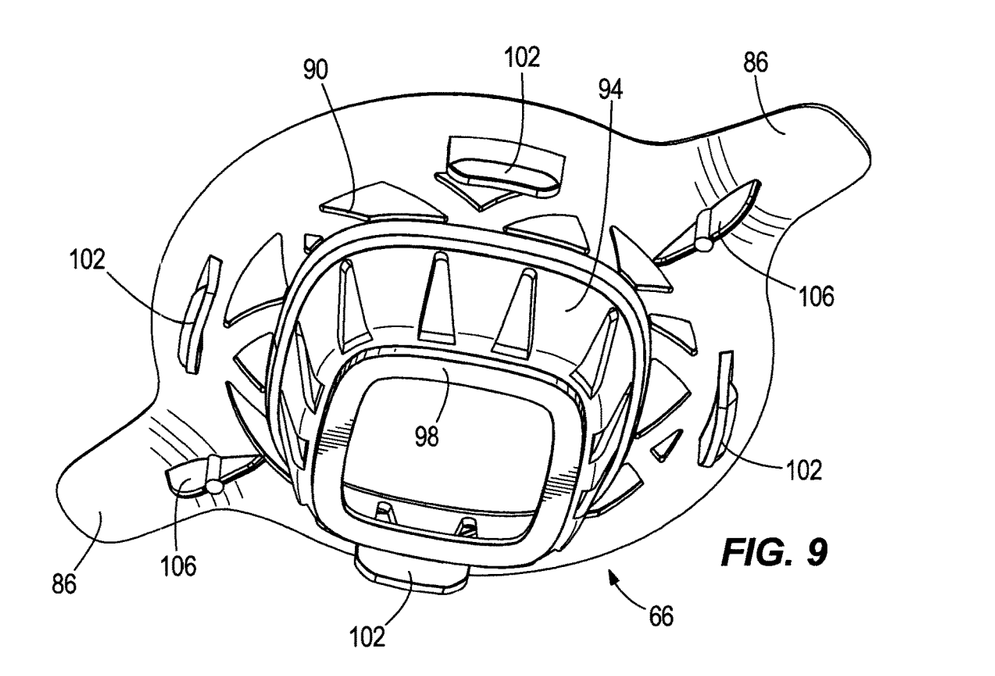
FIG. 9 is a lower perspective view of the upper caddy frame of FIG. 8.

FIG. 9 shows an under side of the upper caddy frame 66 including a lower caddy frame engaging feature in the form of four tabs 102 and two projections or fins 106. In other embodiments, more or less than four tabs 102 and more or less than two fins 106 may be utilized. Additionally, other engaging features may be used (e.g., friction fit, fasteners, adhesive, et cetera) as desired.

Figure 10:
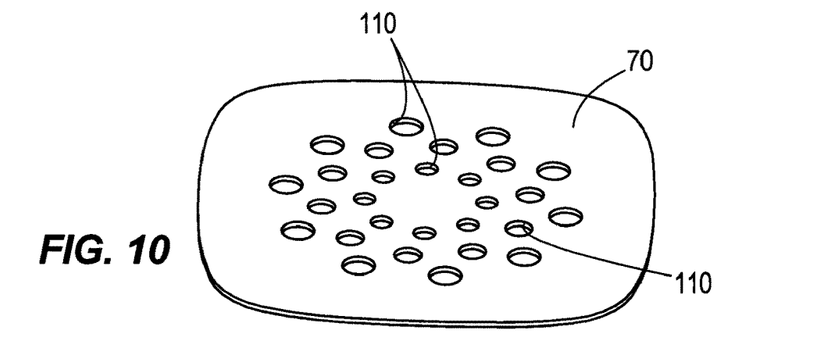
FIG. 10 is an upper perspective view of a heat deflector plate of the caddy assembly of FIG. 7.

The heat deflector plate 70 is shown in FIG. 10 and is sized to be received within the refill receiving cavity 94 of the upper caddy frame 66 and supported on the rim 98. A vent structure in the form of a plurality of holes 110 is formed in the heat deflector plate 70. The illustrated holes 110 are defined by three concentric rings of holes 110. The inner ring defines holes 110 of a first diameter, the middle ring defines holes 110 of a second diameter, and the outer ring defines holes 110 of a third diameter. The holes 110 are sized and arranged to provide a predetermined airflow into the refill receiving cavity 94. Alternatively, the holes may all be of the same size. The heat deflector plate 70 provides a control flow of heat energy toward the substrate 30 and inhibits the overheating or melting of the substrate 30. In other embodiments, the vent structure may be arranged differently. For example, a plurality of slots, or wedge shaped vents may be formed in the heat deflector plate 70, as desired.

Figure 11:
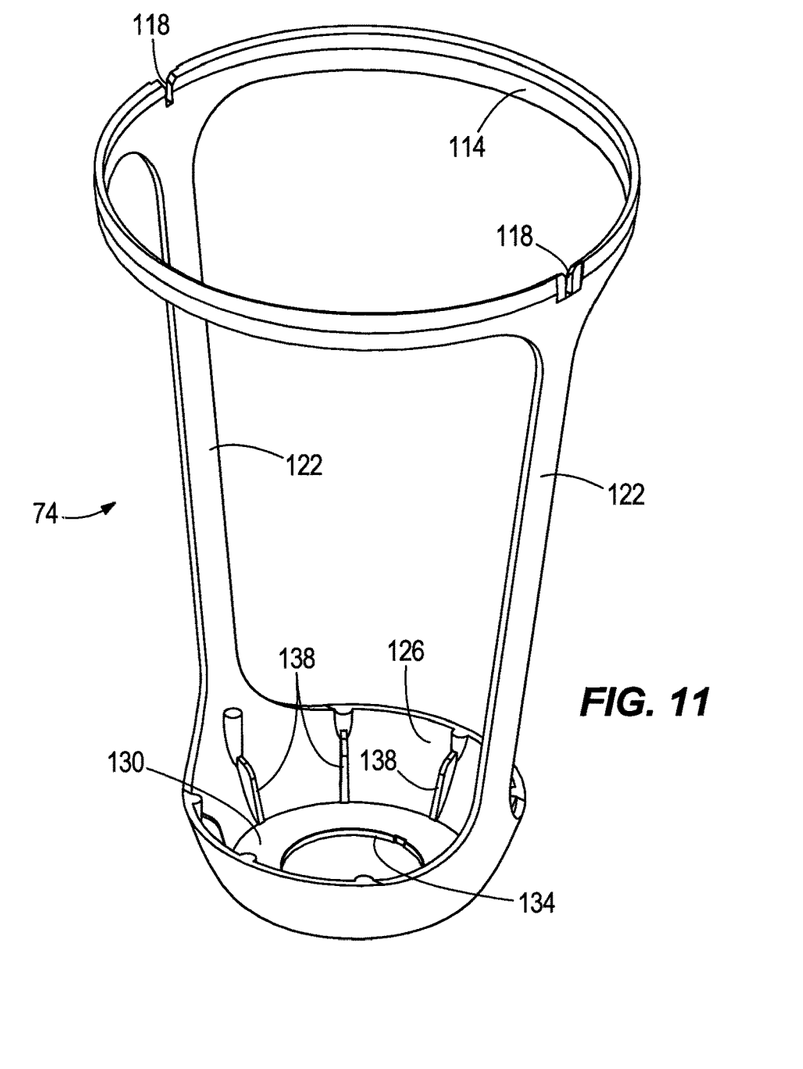
FIG. 11 is an upper perspective view of a candle holder portion of the caddy assembly of FIG. 7 integrally formed with a trapeze hanger structure.

As shown in FIG. 11, the lower caddy frame 74 includes an upper caddy frame mounting feature in the form of a ring 114 sized to be engaged by the tabs 102 of the upper caddy frame 66 and two recesses or slots 118 sized to receive the fins 106 of the upper caddy frame 66.

FIG. 12 shows the tabs 102 engaging the ring 114 (two tabs 102 are visible) and the fins 106 engaging the slots 118 (one fin 106 and slot 118 are visible). When assembled as shown in FIG. 12, the upper caddy frame 66 and the lower caddy frame 74 are substantially rigidly mounted to one another such that there is no substantial movement of one component relative to the other.

The lower caddy frame 74 also includes two extension elements 122 that space a candle holder 126 away form the ring 114. More than two or less than two extension elements 122 may be utilized or the extension elements may have a different shape, so long as they support the candle holder 126 spaced apart from the upper caddy frame 66 when the lower caddy frame 74 and the upper caddy frame 66 are assembled.

The candle holder 126 includes a support surface 130 for supporting the candle 26, an candle aperture 134 formed through the support surface 130, and a centering feature in the form of ribs 138. The support surface 130 provides a solid base that holds the candle 26 when in use. The candle aperture 134 is sized such that a standard tea candle will fall through the candle aperture 134 and not be supported on the support surface 130. The candle 26 is specially designed to operate with the candle dispenser 10 and the candle aperture 134 helps the end user ensure a most appropriate candle 26 is being used such that the candle dispenser 10 can function to its intended potential (e.g. a specified heating range). Specifics of the candle 26 will be discussed below. The ribs 138 maintain the candle 26 in a centered position on the support surface 130.

Figure 13:
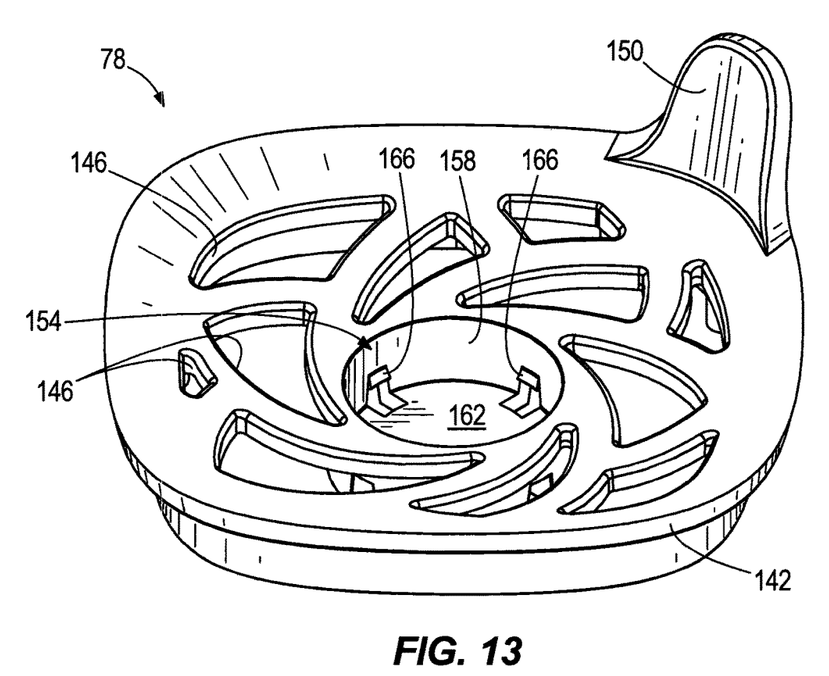
FIG. 13 is an upper perspective view of a refill frame of the caddy assembly of FIG. 7.

As shown in FIG. 13, the refill frame 78 includes a flange 142 sized to be supported on the shoulder 96 of the refill receiving cavity 94, a vent structure in the form of a plurality of apertures 146, a handle 150, and a substrate receiving feature 154. The apertures 146 are sized and arranged to permit a predetermined airflow therethrough. The handle 150 provides an easily graspable feature that allows a user to remove and install the refill frame 78 with ease. In other embodiments, the vent structure may be arranged differently. For example, a plurality of slots, a spiral pattern, or another structure may be utilized to provide the desired airflow. Additionally, the handle 150 may take another form. More than one handle 150 may be formed on the refill frame 78, or positioned on a different area of the refill frame 78, as desired.

The substrate receiving feature 154 includes a sidewall 158, a base or floor 162, and a substrate retaining feature in the form of four tabs 166 (two tabs 166 are visible in FIG. 13). The sidewall 158 is substantially cylindrical, although other shapes are considered to match the desired substrate 30. For example, the sidewall may be square, rectangle, or another shape. In other embodiments, the floor 162 may include apertures or vent features other than the small openings formed near the tabs 166, as desired.

Figure 14:
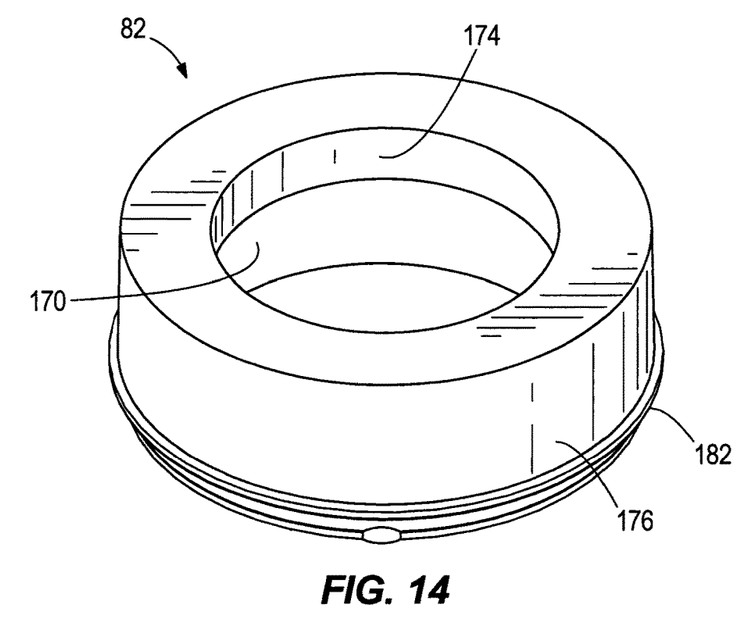
FIG. 14 is an upper perspective view of a refill retainer ring suitable to be used with the FIG. 13 refill frame.

As shown in FIG. 14, the refill retainer 82 includes an interior cavity 170 sized to receive the substrate 30, an upper flange 174 sized to inhibit the substrate 30 from passing therethrough, an outer wall 176 sized to be received within the sidewall 158 of the substrate receiving cavity 154, and a shoulder 182 sized to be engaged by the tabs 166 of the substrate receiving feature 154. The bottom (as shown in FIG. 14) of the refill retainer 82 is open such that the substrate 30 may be received within the interior cavity 170. In other embodiments, the refill retainer 82 may be shaped differently to receive the substrate and mate with the substrate receiving cavity 154. Further, the refill retainer 82 may be eliminated and the substrate 30 maintained in the refill frame 78 by press fit, or another means.

The substrate 30 shown in FIG. 3 is preferably a porous sand core made of sand mixed with novolac (or other resin) binder as well as about 40 milligrams of a pest control active ingredient such as metofluthrin mixed in acetone (e.g., a 30% mixture). In other embodiments the substrate is dosed with between about 25 mg and 150 mg of pest control active ingredient. See generally U.S. Pat. No. 7,820,188 for suitable sand core substrate constructions. The illustrated substrate 30 is generally cylindrically shaped. In other constructions, the substrate may be conically shaped, frusto-conically shaped, square, rounded square, or another shape, as desired.

For purposes of prolonged useful life with effectiveness throughout a relatively large area (e.g. 100 square feet or more), it has been found desirable to configure some of the devices within particular parameters. For example, it has been found desirable for the thickest part of the substrate 30 to be between 0.5 cm and 5 cm thick, preferably about 1 cm thick. In one embodiment, the substrate 30 may be dosed with 25 mg or more of pest control active ingredient (e.g., 70 mg metofluthrin). Metofluthrin tends not to vaporize off of such sand cores absent heating, and has particularly desirable repellency and other characteristics when the substrate 30 is heated to about 120° C. (e.g., 123° C.) at its top surface (about 150° C. at the bottom surface).

One can dissolve the active in acetone or a hydrocarbon before it is dosed on the substrate 30. When the active is applied to the substrate 30 it may be coated on or impregnated in various ways. For example, drops of a mix can be released above the substrate 30 and allowed to disperse through the substrate 30.

Air treatment chemicals to be applied to sand core may include a wide variety of actives. See U.S. Pat. Nos. 6,309,986 and 6,337,080 for disclosure of a variety of insect control materials, deodorizers, fragrances, sanitizers, and disinfectants known to be suitable for use with heating dispensers. For example, suitable active materials may include (when the volatile material is an insecticide and/or insect repellent) organic phosphorous insecticides, lipid-amide insecticides, natural repellents as citronella oil, natural pyrethrins and pyrethrum extract, and synthetic pyrethroids. Suitable synthetic pyrethroids include without limitation acrinathrin, allethrin as D-allethrin, Pynamin, benfluthrin, bifenthrin, bioallethrin as Pynamin Forte, S-bio-allethrin, esbiothrin, esbiol, bioresmethrin, cycloprothrin, cyhalothrin, lambda-cyhalothrin, cyphenothrin, empenthrin, esfenvalerate, fenpropathrin, fenvalerate, flucythrinate, tau-fluvalinate, kadethrin, metofluthrin, phenothrin, prallethrin as Etoc, resmethrin, tefluthrin, tetramethrin, or transfluthrin. It is preferred to use a highly volatile active when seeking insect control in a large space or outdoors on a patio. It is most preferred to use metofluthrin or transfluthrin when mosquito control is of primary interest in a large outdoor area.

As shown in FIG. 2, the candle 26 includes a cup 186, a wax 190, and a wick 194. The shape of the candle generally reflects the shape of the lower portion of the caddy 22 and is substantially different than the shape of the upward opening of the upper caddy frame 66, such that a user is not confused about where the candle is to be mounted. The cup 186 defines a diameter larger than a standard tea candle such that the candle 26 does not fall through the candle aperture 134 of the lower caddy frame 74 but is supported on the support surface 130. In this way, a user of the candle dispenser 10 is aided in avoiding the use of non-genuine candles (which might provide too little heat to be fully effective). The diameter of the cup 186 also provides that the ribs 138 substantially center the candle 26 with respect to the caddy 22.

The wax 190 is preferably a mix of conventional candle waxes, but presented in a diameter slightly wider than a standard tea candle size. Optionally, another secondary air treatment chemical (e.g., a fragrance, citronella) may be mixed directly in with the wax 190. This wax mix, together with a cotton or other wick 194, generates a very desirable temperature range for the present purposes.

Assembly of the candle dispenser 10 will next be discussed. As shown in FIG. 1, the housing 14 and the base 18 are assembled by engaging the tabs 38 of the housing 14 with the recesses 54 of the base 18 to form a substantially rigid structure. In other embodiments, the housing 14 and the base 18 may be formed as a single structure or may include additional components, as desired.

As shown best in FIGS. 7 and 9, the caddy 22 is assembled by aligning the fins 106 of the upper caddy frame 66 with the slots 118 of the lower caddy frame 74 and engaging the tabs 102 of the upper caddy frame 66 with the ring 114 of the lower caddy frame 74 (see also FIG. 12). The heat deflector plate 70 is then dropped onto the rim 98 of the upper caddy frame 66 (see also FIG. 2). The refill frame 78 is inserted into the refill receiving cavity 94 and supported on the shoulder 96, the substrate 30 is dropped into the substrate receiving feature 154, and the refill retainer 82 is engaged with the substrate receiving feature 154 to lock the substrate 30 in place. The candle 26 is then deposited onto the candle holder 126 by the consumer.

With reference to FIG. 2, the completed caddy 22 is then inserted into the housing 14 such that the lift handles 86 are supported on the caddy recesses 50 of the housing 14.

When the candle dispenser 10 is assembled, the candle 26 is spaced apart from the table or other surface the candle dispenser 10 is resting on such that the candle dispenser 10 may be used even on heat sensitive surfaces. A distance "A" between the candle 26 and the substrate 30 is fixed, as is the distance between the heat deflector plate 70 and the substrate 30. For example, the distance "A" from a top of the candle 26 to a bottom of the substrate 30 may be between 60 mm and 105 mm (e.g., about 95 mm on average).

In addition to the fixed distances, the controlled airflow (e.g., via the various vents and air inlets) maintains the substrate at a remarkably controlled temperature. For example, the substrate 30 may be maintained at approximately 120° C. at a top surface and 150° C. at a bottom surface. At a temperature between 100° C. and 150° C. a substantially consistent level of active release can be achieved for one or more hours. To achieve even better performance beyond six hours (e.g., eight hours over portions of two days) one may trim the wick 194 after use on the first day (e.g., after about four hours).

The various vents/inlets in the candle dispenser 10 are preferably sufficiently small that the candle 26 is unlikely to be accidentally snuffed out by a draft caused by a person walking rapidly by the candle dispenser 10, or by typical wind experienced in patio areas. However, they are large enough to provide sufficient air to the candle 26 to support the flame, disperse heat spikes, and permit dispensing of the active.

When the candle 26 and/or the substrate 30 is used up, the caddy 22 can be lifted out of the housing 14 by the lift handles 86. As will be apparent from FIG. 15, a new candle 26 may be placed in the candle holder 126 and the caddy 22 replaced into the housing 14. To replace the substrate 30, a user may remove the refill upper caddy frame 66 and replace with a new refill upper caddy frame 66 including a new substrate 30 and a new refill retainer 82. The subassembly of the refill upper caddy frame 66, substrate 30, a refill retainer 82, and candle 26 may be purchased as a packaged kit as suggested by the bracketed portion of FIG. 15. Alternatively, only the substrate 30 may be replaced.

Most preferably, the substrate 30 and candle 26 are designed to operate in the candle dispenser 10 with a matching lifespan. That is to say, the candle 26 and substrate 30 are intended to last about the same duration (e.g., 4, 6, or 8 hours) while producing an effective 7-10 mg/hour release rate of the active in the substrate 30. The synchronized duration of the candle 26 and the substrate 30 simplifies the users understanding of when a refill kit is required. In other words, when the user sees the candle 26 is burned out, it is communicated that the candle 26 and the substrate 30 are spent and a new refill kit should be installed.

Figure 15:
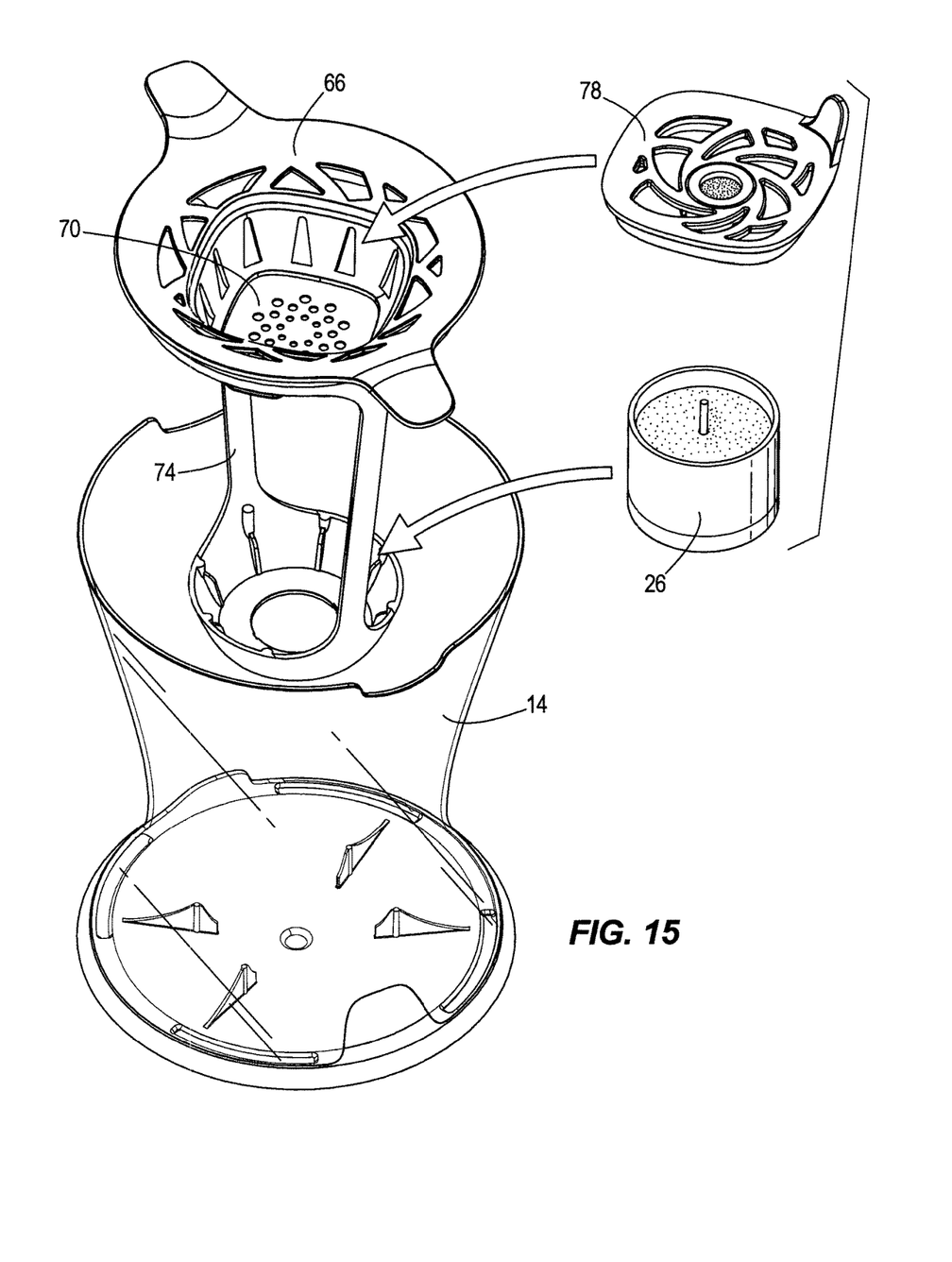
FIG. 15 is an exploded view of the device of the present invention in process of being assembled, with a refill kit portion thereof being highlighted.

As shown in FIG. 15, a substrate 30 supported on the refill frame 78 and a candle 26 can be intuitively used as a refill kit. In a preferred embodiment, proper alignment of the two pieces of the refill kit may be achieved by matching the shape of the refill frame 78 to the shape of the receiving area in the upper caddy, and matching the shape of the candle 26 to the shape of the candle holder.

It will be appreciated that the lower caddy frame 74 helps drop the candle into an appropriate positioning which is further aligned by fins 58 of the base. Also, lift handles 86 then are dropped down into recesses 50 of the outer housing completing the desired alignment.

In sum, the present invention achieves via various embodiments (at low cost) effective and consistent mosquito repellent protection for a relatively large area over a prolonged period. While the above describes preferred embodiments of the present invention, other embodiments are also within the intended scope of the invention. For example, alternative binders can be used in a sand core as described in U.S. Pat. No. 7,820,188 (urethane resins; highly crossed linked thermoplastics). Thus, the invention is not to be limited to just the specific embodiments shown or described herein, and the following claims should be looked to in order to judge the full scope of the invention.

INDUSTRIAL APPLICABILITY

Disclosed herein are improved candle dispenser devices, and refill kits used therewith, particularly those designed to control insects over prolonged periods throughout large areas such as patios.

All documents cited in this patent are, in relevant part, incorporated herein by reference. The citation of any document is not to be construed as an admission that it is prior art with respect to the present invention.

What is claimed is:

1. A device for dispensing an air treatment chemical, the device comprising:
   a housing having a side wall defining a first internal cavity;
   a caddy assembly supported by the housing and having:
      an upper caddy frame having an upper surface and a second sidewall defining a second internal cavity, the second sidewall depending downwardly from the upper surface, wherein the second internal cavity is configured to mount a substrate bearing an air treatment chemical adjacent an upper portion of the housing; and
      a candle holder removably coupled to the upper caddy frame and configured to support a candle having a wick adjacent a lower portion of the housing in the first internal cavity;
   a substrate bearing air treatment chemical suitable to be supported by the upper caddy frame; and
   a candle suitable to be supported by the candle holder.

2. The device of claim 1, further comprising a heat deflector plate arranged between the substrate and candle holder.

3. The device of claim 2, wherein the heat deflector plate has a vent structure.

4. The device of claim 1, further comprising a base coupled to the housing that can align the candle holder with respect to the housing.

5. The device of claim 1, wherein the housing has a wide upper portion, a middle portion less wide than the upper portion, and a lower portion more wide than the middle portion.

6. The device of claim 1, wherein the candle holder can be positioned in the housing by repositioning the upper caddy frame.

7. The device of claim 1, wherein the caddy assembly further comprises a trapeze form hanger between the upper caddy frame and the candle holder.

8. The device of claim 1, further comprising a refill frame for supporting the substrate.

9. The device of claim 8, wherein the heat deflector plate is supported by the upper caddy below the refill frame.

10. The device of claim 8, wherein the upper caddy frame has a first internal circumference geometry configured to accommodate a shape of the refill frame supporting the substrate, wherein the candle holder has a second internal circumference geometry configured to accommodate a shape of the candle, and wherein the first internal circumference geometry differs in shape from the second internal circumference geometry.

11. The device of claim 1, wherein the substrate can release at least 6 mg per hour of the air treatment chemical when the candle is lit.

12. The device of claim 1, wherein the candle is configured to be able to heat a bottom of the substrate for over a consecutive hour to between 115 degrees C. and 160 degrees C., and when this occurs a top of the substrate can be maintained between 115 degrees C. and 135 degrees C. throughout that hour.

13. The device of claim 11, wherein the air treatment chemical is a pest control active ingredient and the substrate comprises a sand core.

14. The device of claim 13, wherein the sand core substrate is impregnated with the pest control active ingredient and the candle is positioned below the sand core substrate.

15. The device of claim 14, wherein a distance between a top of the candle and a bottom of the substrate is from 60 mm to 105 mm.

16. The device of claim 14, wherein a heat deflector plate is positioned between the substrate and the candle, and wherein the heat deflector plate includes a plurality of vent holes.

17. The device of claim 16, wherein the plurality of vent holes in the heat deflector plate are all the same size.

18. The device of claim 16, wherein the plurality of vent holes in the heat deflector plate are arranged with smaller holes toward a center of the heat deflector plate and larger holes positioned radially outwardly from the smaller holes.

19. The device of claim 1, wherein the upper caddy frame has two handles, and a top of the housing has two recesses adapted to receive the two handles when the caddy assembly is lowered into the first internal cavity of the housing.

* * * * *